United States Patent [19]

Höelzler

[11] 4,164,213
[45] Aug. 14, 1979

[54] APPARATUS FOR EXAMINING BODIES THROUGH SCANNING BY MEANS OF ULTRASOUND

[75] Inventor: Georg Höelzler, Moehrendorf, Fed. Rep. of Germany

[73] Assignee: Siemens Aktiengesellschaft, Berlin & Munich, Fed. Rep. of Germany

[21] Appl. No.: 799,970

[22] Filed: May 24, 1977

[30] Foreign Application Priority Data

Jun. 25, 1976 [DE] Fed. Rep. of Germany ....... 2628492

[51] Int. Cl.² .................................................. A61B 10/00
[52] U.S. Cl. .................................................... 128/660
[58] Field of Search ............... 128/2 V, 2.05 Z, 24 A; 73/607, 618, 619, 620, 621, 625, 626, 628

[56] References Cited

U.S. PATENT DOCUMENTS 4,064,741  12/1977  Reynolds ............................... 73/620

*Primary Examiner*—William E. Kamm

*Attorney, Agent, or Firm*—Hill, Van Santen, Steadman, Chiara & Simpson

[57] ABSTRACT

In the illustrated embodiments, successive overlapping groups of ultrasonic transducer elements are activated to scan along successively offset group symmetry axes. The groups may be selected so that the active symmetry axis is shifted in increments of one-half the element width with a first set of symmetry axes coinciding with a gap between adjacent transducer elements and a second set coinciding with the center of a transducer element. In other embodiments, the successive groups of the first type are sequentially activated in a first cycle and the successive groups of the second type are sequentially activated in a second cycle to produce scanning along interlaced sets of symmetry axes and to produce twice the image display rate. The groups of transducer elements of the first and second types may comprise even and odd numbers of adjacent elements, respectively; or elements which are variously spaced from the symmetry axis may be simultaneously energized to increase the number of scanning lines in relation to the number of transducer elements.

10 Claims, 6 Drawing Figures

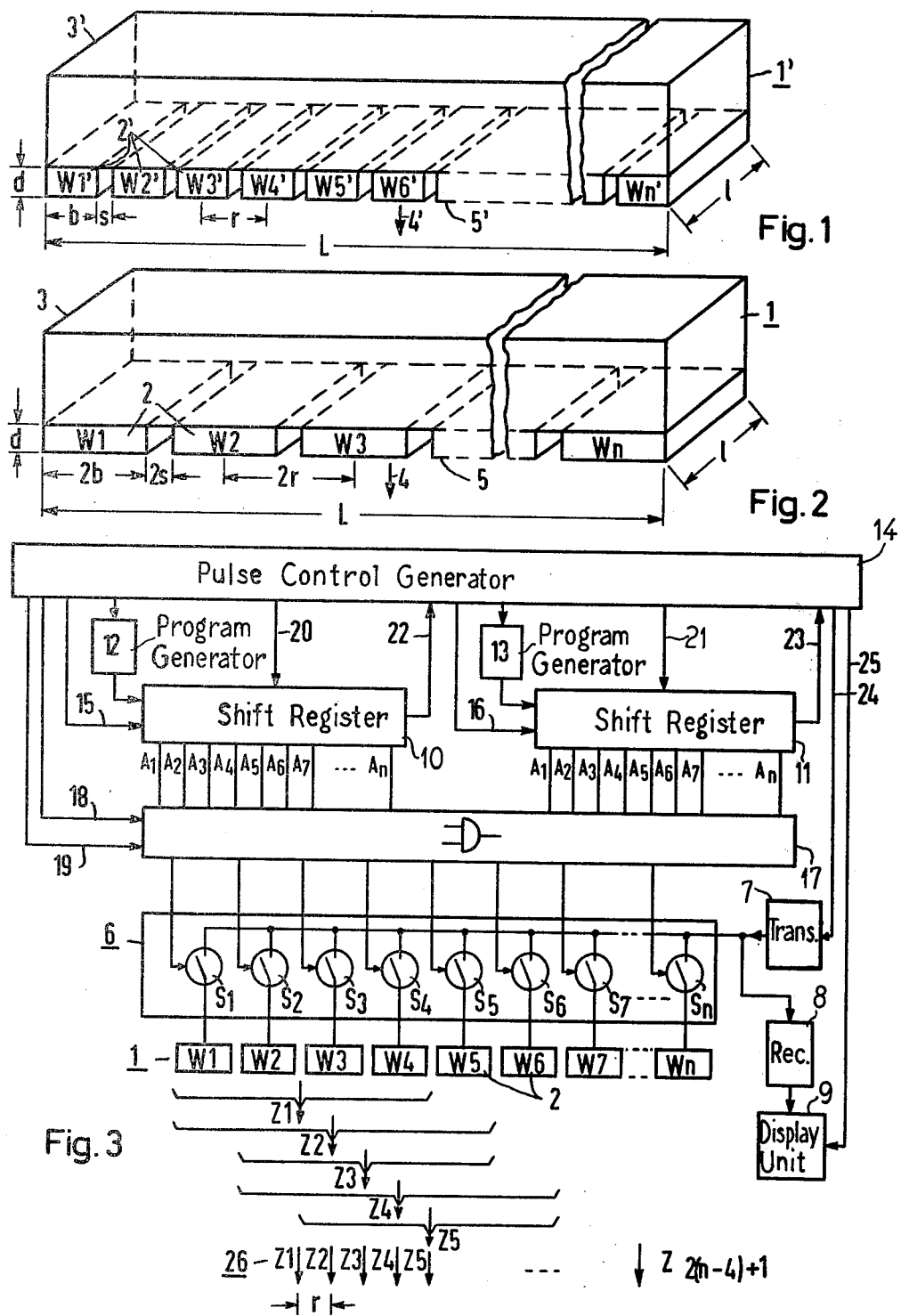

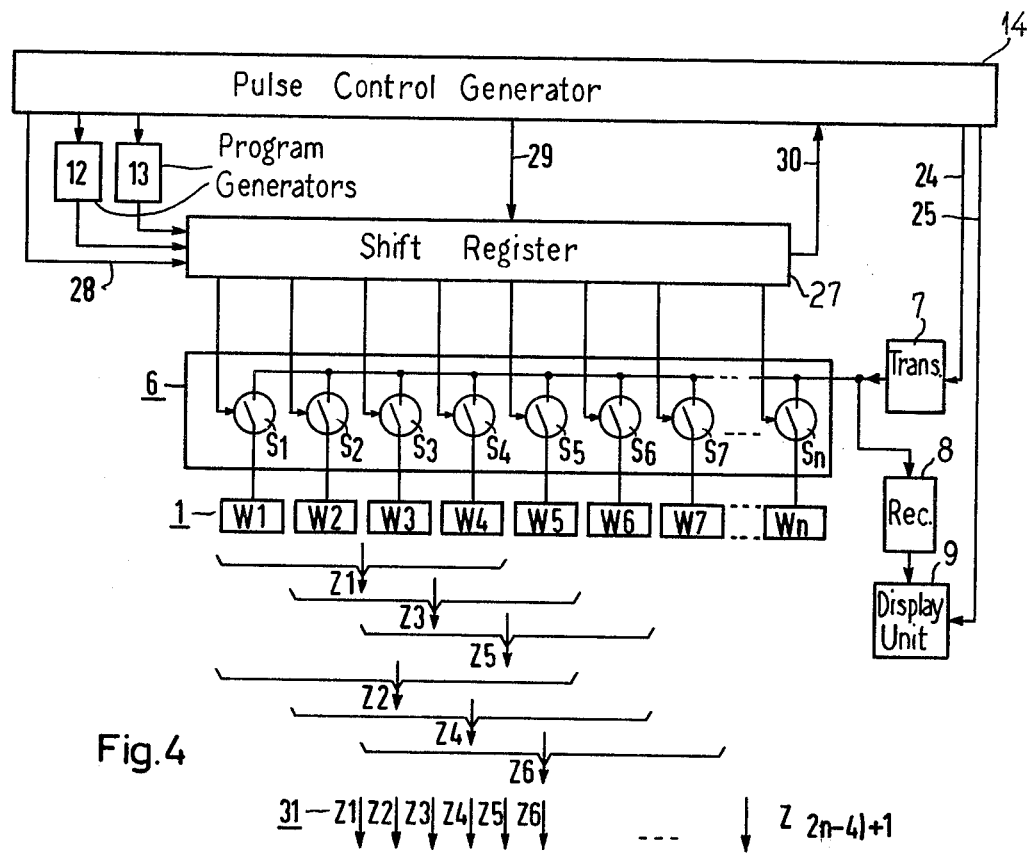
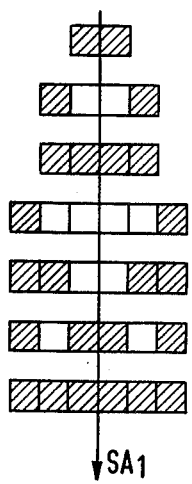
Fig.5
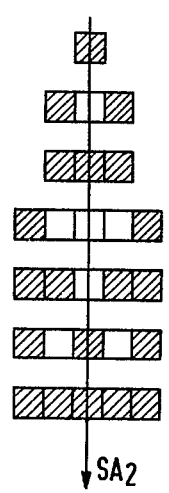
Fig.6

APPARATUS FOR EXAMINING BODIES THROUGH SCANNING BY MEANS OF ULTRASOUND

BACKGROUND OF THE INVENTION

The invention relates to an apparatus for examining bodies through scanning by means of ultrasound, comprising an ultrasonic applicator with at least one row of adjacent ultrasonic transducer elements and an actuating mechanism for the purpose of actuating the transducer elements individually or in groups.

An apparatus of this type is prior art e.g. from the U.S. Pat. No. 3,881,466. The ultrasonic applicator of this apparatus comprises a row of adjacent ultrasonic elements which are actuated by means of an actuating mechanism in such a manner that successively offset groups of adjacent transducer elements are sequentially energized to produce a scanning cycle. The number of energized transducer elements in one group is of a constant equal magnitude, respectively, and the step size corresponds to the raster distance between two adjacent transducer elements, since the excitation proceeds in each instance by connecting a new transducer element while simultaneously disconnecting the first transducer element of each individual group. Due to this special type of actuating mechanism, there thus results during the ultrasonic scanning a number of lines maximally corresponding to the total number of the transducer elements of the applicator. Since the resolution capability is to be as great as possible, the line density must correspondingly also be selected to be large. In the case of a specified total length of the ultrasonic applicator, this necessitates a relatively large number of transducer elements of narrow width; i.e., corresponding to the small raster distance. However, in the case of a large number of transducer elements, there result relatively unfavorable capacitance ratios between the transducer elements and the electronic actuating switches for the elements. These unfavorable capacitance ratios bring about an increased attenuation of the received echo signals, as well as a lower signal-to-noise ratio between the through-connected and disconnected transducer elements. Due to the small raster distance of the transducer elements, in addition, the width/thickness ratio of the individual transducer elements also becomes unfavorable in the sense that increased stray cross-couplings result. On the one hand, this leads to crosstalk between adjacent transducer elements, and, in addition, it leads to unfavorable oscillation ratios, since the interference effect of the undesired lateral oscillation is increased as compared with the desired thickness oscillation. In addition, there are also disadvantages from a technical-manufacturing viewpoint, since, if the number of transducer elements is increased, the number of required soldering locations is correspondingly great, and there are also resulting disadvantages in the electronic outlay, since a relatively large number of transducer elements leads to a corresponding large number of electronic actuating switches, a relatively high consumption of space and a relatively great cost.

SUMMARY OF THE INVENTION

The object of the invention is to construct an apparatus of the type initially cited which altogether avoids the disadvantages of the known apparatus.

In accordance with the invention, the object is achieved by virtue of the fact that the actuating mechanism for actuating the transducer elements of the ultrasonic applicator is constructed in different symmetrical configurations of transducer elements such that the symmetry axes of the configurations of simultaneously energized transducer elements, in one type of configuration, become placed in the gap between two adjacent transducer elements, and, in another type of configuration, in the center of a transducer element, whereby the actuation proceeds in such a manner that, in the course of a scanning cycle over the entire length of the applicator, the symmetry axes occupy, at least once, every possible position in the gaps between two transducer elements, or in the centers of the transducer elements, with the possible exception of only the transducer elements of the first half of the first, and the second half of the last transducer element group of the applicator.

With the apparatus according to the invention, it is possible to realize line spacings in the ultrasonic scanning which no longer correspond to the entire, but only to half the raster distance between adjacent transducer elements. What is achieved hereby is that, in the case of a given number of transducer elements on the ultrasonic applicator, there is double the number of lines, or, conversely, in the case of a given number of lines, there is half the required transducer elements as compared with the conventional applicators. The latter instance, however; i.e., reduction in the number of the transducer elements by one-half while maintaining the same overall length of the ultrasonic applicator, and without changing the number of lines, renders possible an enlargement e.g. the doubling of the transducer width of each element with a simultaneous widening e.g., also a doubling, of the intermediate space between two adjacent transducer elements. This results in the advantage that, due to the enlarged e.g. doubled ratio of width/thickness of each transducer element, there is a lesser occurrence of cross-coupling between the transducer elements, because the frequency spacing between the desired thickness oscillation and the undesired width oscillation of each element becomes greater, and thus the interfering influence of the width oscillation is reduced. Due to the enlarged intermediate spaces between the individual transducer elements, the danger of a crosstalk between adjacent transducer elements is also considerably reduced. The reduced total number of all the transducer elements for a given applicator size further results in substantially improved capacitance ratios, causing the received echo signals to be less strongly attenuated and the signal-to-noise ratio between throughconnected and disconnected transducers to be increased. When the number of transducers is reduced by half, there is also a resulting more rapid and simpler soldering, on account of the larger-area construction (or design) of the transducer elements, and the number of required actuating switches is further reduced by half. Thus, the manufacturing-technical and electronic advantages of the invention are obvious.

Other objects, features and advantages of the invention will be apparent from the following detailed description of certain illustrative embodiments, taken in connection with the accompanying sheets of drawings.

BRIEF DESCRIPTION OF THE DRAWINGS

FIG. 1 illustrates an ultrasonic applicator in a conventional embodiment;

FIG. 2 illustrates an ultrasonic applicator in an embodiment according to the present invention;

FIG. 3 illustrates a first embodiment of actuating mechanism for producing scanning by means of the ultrasonic applicator of FIG. 2, by means of a basic electric circuit diagram;

FIG. 4 illustrates a second embodiment of actuating mechanism for producing scanning operation of the ultrasonic applicator of FIG. 2 by means of an interlaced scanning method; and FIGS. 5 and 6 illustrate various examples of different symmetrical transducer configurations for producing symmetry axes coinciding with a gap between transducer elements and for producing symmetry axes coinciding with the center of a transducer element, respectively.

DETAILED DESCRIPTION

In FIG. 1, the conventional ultrasonic applicator $1'$ consists e.g. of a number of $n'=108$ individual transducer elements $W_1'$ through $W_n'$, which are adjacently supported in a row $2'$ on a carrier section $3'$. Carrier section $3'$ consists of a material which readily absorbs the ultrasound; i.e., epoxy resin. Accordingly, in the operating state, ultrasonic scanning proceeds only along paths parallel to direction arrow $4'$ perpendicular to the application surface $5'$ of applicator $1'$. Transducer elements $W_1'$ through $W_n'$ of the conventional ultrasonic applicator $1'$ are preferably formed of small piezoelectric crystal plates which for operating frequencies e.g. in the range of approximately 4 MHz manifest a thickness $d=0.5$ mm, a width $b=0.9$ mm and a length $l=8$ mm. The gap width s between the individual small transducer plates is $s=0.1$ mm. Thus, a raster distance of $r=$one millimeter (1 mm) results. Thus, given a total number of transducer elements $n'=108$, the total length of the applicator $1'$ is $L=108$ mm. Upon actuating the transducer elements e.g. in quadruplets (or groups of four), with advance by one transducer element with each ultrasonic pulse, respectively, there is a resulting line number of approximately 105 lines per ultrasonic image, the lines for the two first elements $W_1'$, $W_2'$, and the two last elements $W_n'$- $1'$, $W_n'$, of the transducer row being suppressed, since preferably only complete quadruplets (or groups of 4) are to contribute to the line scanning process.

In the case of ultrasonic applicator 1 in the inventive embodiment according to FIG. 2, small piezoelectric crystal plates again act as transducer elements $W_1$ through $W_n$, which, corresponding to FIG. 1, are adjacently arranged in a row 2 on a carrier section 3. Carrier section 3 is constructed according to that of FIG. 1, so that there is again a radiation direction 4 resulting which is perpendicular to the application surface 5 of applicator 1. Small crystal plates $W_1$ through $W_n$ of transducer row 2 have a thickness $d=0.5$ mm and length $l=8$ mm, corresponding to the small crystal plates $W_1'$ through $W_n'$ of transducer row $2'$ of applicator $1'$. However, in contrast with the small crystal plates $W_1'$ through $W_n'$, the width of the small crystal plates $W_1$ through $W_n$ is twice as great; i.e., 2b or 1.8 mm. The gap distance is correspondingly enlarged; i.e., it amounts to e.g. 2s or 0.2 mm. The raster distance of the small plates is thus also doubled; i.e., to 2r or 2 mm. Given an overall length of applicator 1 of again approximately $L=108$ mm, there is thus a total number of required transducer elements of $n=54$. However, in spite of the fact that there is only half the number of transducers with applicator 1 according to FIG. 2, there is again approximately the same number of lines as in the case of the applicator according to FIG. 1; i.e., precisely 101 lines per complete ultrasonic image given an assumed quadruplet—or quintuplet—shift rhythm, such as shall be further explained in the following on the basis of FIGS. 3 and 4.

In FIGS. 3 and 4, ultrasonic applicator 1 is constructed corresponding to that of FIG. 2; i.e., it again comprises a transducer row 2 with a total of preferably fifty-four transducer elements. However, only the first seven transducer elements $W_1$ through $W_7$, as well as the n-th (i.e., the 54th) transducer element $W_n$ are illustrated. A number of actuating switches $S_1$ through $S_n$—corresponding to the number of transducer elements—of a switch bank 6 serves the purpose of actuating the individual transducer elements $W_1$ through $W_n$ of transducer row 2. Each switch $S_1$ through $S_n$, in the closed state, connects the respective transducer element $W_1$ through $W_n$ associated with it to a high frequency pulse transmitter 7 in transmitting operation (or transmit mode) or to an echo signal signal receiver 8 in the receiving operation (or receiving mode). A display unit 9 serves the purpose of rendering visible the echo signals in to form of an echo sectional image; this display unit being, for example, an electron beam tube (cathode ray tube). The latter display unit effects the reproduction of the echo signals obtained in line-by-line fashion from the subject under examination, said reproduction proceeding in a correspondingly linear fashion as bright spots on a display screen by means of brightness modulation.

In the basic circuit diagrams according to FIGS. 3 and 4, the actuation of transducer elements $W_1$ through $W_n$ of transducer row 2 differs in that, in the case of the sample embodiment according to FIG. 3, a continuous excitation of the transducer element takes place alternately in groups of four and five transducer elements; by way of contrast, the basic circuit diagram according to FIG. 4 operates according to the interlaced scanning method; i.e., the excitation of the transducer elements proceeds continuously over the transducer row 2; for example, first in groups of four respective transducer elements (first image subframe), and, in the following, beginning anew in groups of five respective transducer elements (second image subframe). Accordingly, the basic circuit diagrams according to FIGS. 3 and 4 differ somewhat in the actuating electronics. Thus, e.g., the sample embodiment according to FIG. 3 comprises a total of two shift registers 10 and 11 with one associated group program transmitter 12, or 13, each. Group program transmitter 12 is adjusted such that, at the beginning of each scanning, it delivers to shift register 10 a quadruplet of set pulses, respectively, which are then always further shifted (or advanced) by one register location in shift register 10 in response to each shifter pulse of a central pulse control generator 14. Line 15 serves the purpose of supplying the shifter pulses of pulse control generator 14 to shift register 10. In a corresponding fashion, group program generator 13 produces a quintuplet of individual impulses for shift register 11, which, in turn, are further shifted (or advanced) by one position in shift register 11 in the cadence (or rhythm) of the shifter pulses of pulse control generator 14 supplied to shift register 11 via shifter pulse line 16. The actuation of the individual switches $S_1$ through $S_n$ of switch bank 6 proceeds in dependence upon the output signals of shift registers 10 or 11 via gate logic 17 which always connects the shift register outputs $A_1$ through $A_n$ of the respective shift register 10 or 11 with the control inputs of switches $S_1$ through $S_n$ when through-connection pulses of pulse control generator 14 are supplied to gate logic 17 via switching inputs 18 or 19. Gate logic 17 is so conceived that, with the occurrence of a through-connection pulse on through-connection input 18, shift register 10 is connected at its output side with the control inputs of switches $S_1$ through $S_n$, whereas with the occurrence of a through-connection pulse on through-connection input 19 of gate logic 17, on the other hand, a connection is established between the control inputs of the switches and the signal outputs of shift register 11. The respective through-connection pulses of gate logic 17, as previously indicated, are supplied by the pulse control generator 14. Correspondingly, pulse control generator 14 also produces reset pulses for shift registers 10, 11 via reset lines 20, 21, as soon as the end of a pulse cycle of the impulse groups through the respective shift registers 10, 11 is communicated back via return signal lines 22, 23. Control lines 24 and 25 provide pulse transmitter 7 and display unit 9 with control signals of the pulse control generator 14 for the transmitting receiving cycles; i.e. for the echo-image formation.

As previously indicated, in the basic circuit diagram according to FIG. 3 the advance switching of transducer elements $W_1$ through $W_n$ proceeds in a step-by-step fashion alternating in groups of four and groups of five. The initiation of each scanning is thus determined such that a control pulse is delivered via the pulse control generator 14 to the group program transmitter 12, which subsequently counts into shift register 10 a combination consisting of four individual pulses. As soon as this counting-in operation has been terminated, a through-connection pulse is supplied from pulse control generator 14 to gate logic 17 via through-connection input 18. This through-connection pulse connects outputs $A_1$ through $A_n$ of shift register 10 with the control inputs for the switches $S_1$ through $S_n$. Since, in the case of shift register 10, only the first four outputs $A_1$ through $A_4$ are set, accordingly only switches $S_1$ through $S_4$ are closed. Once this operation is completed, impulse transmitter 7 is activated via control line 24 for the purpose of producing a high frequency pulse. This high frequency pulse is delivered via the closed switches $S_1$ through $S_4$ to transducer elements $W_1$ through $W_4$. The latter are energized in equiphase-fashion and an ultrasonic pulse is radiated which scans a (non-illustrated) subject under examination in a scanning line corresponding to directional arrow $Z_1$. After conversion into corresponding electrical signals by the transducers $W_1$ through $W_4$, the echo signals originating from this line are then transmitted to echo signal-receiver 8 via the still-closed switches $S_1$ through $S_4$, and, from this echo signal-receiver 8, they are delivered to display unit 9 for the purpose of recording in the form of a corresponding echo signal line. With the termination of this first transmitting-receiving period, the through-connection pulse on through-connection line 18 disappears and switches $S_1$ through $S_4$ are thus again opened. Simultaneously, however, pulse control generator 14 activates group program generator 13, which subsequently counts a group of five individual pulses into shift register 11. As soon as this counting-in operation is completed, an additional through-connection pulse is delivered via through-connection input 19 to gate logic 17, said through-connection impulse now connecting outputs $A_1$ through $A_n$ of shift register 11 with the control inputs of switches $S_1$ through $S_n$. Since, of all the outputs $A_1$ through $A_n$ of shift register 11, only outputs $A_1$ through $A_5$ are set, switches $S_1$ through $S_5$ are thus now closed. Upon closing of these switches, the pulse transmitter is again activated via control line 24 for the purpose of delivering an additional high frequency pulse. Due to this high frequency pulse, transducer elements $W_1$ through $W_5$ are now simultaneously equiphase-activated. An ultrasonic scanning pulse results which scans the subject under examination in a line direction $Z_2$. The direction of this arrow $Z_2$ runs through the center of transducer element $W_3$. The echo signals received from this line are again delivered to the display unit 9 via echo receiver 8 for the purpose of visual representation. At the end of this second transmitting/receiving period, the through-connection pulse on through-connection line 19 again disappears. Switches $S_1$ through $S_5$ are thus opened. Simultaneously, a control pulse is supplied by pulse control generator 14 to the shifter pulse input 15 of shift register 10. The pulse-quadruplet located in shift register 10 is thus advanced by one register location. At the end of this pulsing operation, there is a renewed delivery of a through-connection pulse via through-connection line 18 to gate logic 17. Outputs $A_1$ through $A_n$ of shift register 10 are thus again connected to the control inputs of switches $S_1$ through $S_n$. Since, however, only outputs $A_2$ through $A_5$ of shift register 10 are now set, accordingly also only switches $S_2$ through $S_5$ are closed. Thus, via started [-up] impulse transmitter 7, there is a resulting excitation of transducer elements $W_2$ through $W_5$, and a line scanning in the direction of line arrow $Z_3$. With the completion of this third scanning operation, there follows a further pulsing, also by one register position, of the pulse-quintuplet in shift register 11. The repeated through-connection of gate logic 17 via through-connection input 19 closes switches $S_2$ through $S_6$, so that excitation of transducer elements $W_2$ through $W_6$ and consequent line scanning in the direction of line arrow $Z_4$ takes place. The described cycle; i.e., the alternate further (or advance) pulsing of the quadruplet-impulse group in shift register 10, or if the quintuplet-impulse group in shift register 11, as well as the subsequent corresponding through-connection of gate logic 17 is repeated until the quadruplet pulse group in the case of shift register 10, and the quintuplet pulse group in the case of shift register 11 respectively, reach the output of shift register 10 or 11. In this instance, the scanning operation is terminated with the excitation of the last four, or the last five, transducer elements of transducer row 2 of applicator 1, the shift registers 10 or 11, respectively, are reset and the scanning operation is resumed again from the beginning by renewed insertion of pulses into shift register 10 or 11, and renewed resumption of the cyclical further (or advance) pulsing. As indicated in FIG. 3, the result of this periodically advancing scanning is a scan line field 26 consisting of scan lines whose mutual spacing from one another corresponds, respectively, to half the raster width of transducer elements $W_1$ through $W_n$. Thus, given a number of n=54 transducer elements, there is a resulting line raster for each ultrasonic image which is constructed from a total of $2(n-4)+1=101$ lines. Thus, with half the number of transducer elements as compared with conventional ultrasonic applicators, substantially the same number of lines results. The same number of lines, however, results also with the sample embodiment according to FIG. 4 which, as previously mentioned, operates according to the interlaced scanning method.

In order to produce both subframe images, the sample embodiment according to FIG. 4 comprises only one single shift register 27, with which is associated group program generators 12 and 13 for inserting quadruplets and quintuplets of set pulses. Reference numeral 28 designates a shifter pulse line for shift register 27, via which shifter timing pulses of pulse control generator 14 can be supplied to shift register 27. Lines 29 and 30 represent the reset-and revertive-communication line for shift register 27. In the sample embodiment according to FIG. 4, both ultrasonic subframe images are produced in such a manner that first the entire transducer formation $W_1$ through $W_n$ of ultrasonic applicator 1 is progressively pulsed-through in quadruplet formation in a first cycle whereas, in the respective following second cycle, through-pulsation takes place in quintuplet formation. In order to execute the quadruplet pulse rhythm, a pulse-quadruplet is delivered to shift register 27 via group program generator 12, at the beginning of the recording of the first subframe image. This pulse-quadruplet is then further pulsed by one position in the shift register in the cadence of the shifter timing pulses-supplied via shifter pulse line 28—of pulse control generator 14. Due to this through-pulsing of the quadruplet in shift register 27, a corresponding advancing through-connection of switches $S_1$ through $S_n$ in quadruplets results, and a consequent corresponding advancing excitation of transducer elements $W_1$ through $W_n$, likewise in quadruplets. The result is a first subframe image of the ultrasonic scanning comprising only the odd-numbered lines $Z_1$, $Z_3$, $Z_5$, etc. of the sweep raster of a full image frame representation. After construction of the first subframe image, there is a switchover to scanning in the second subframe image proceeding in such a manner that a quintuplet of set pulses in now fed into shift register 27 via group program generator 13. The following through-pulsing of this quintuplet in shift register 27 effects a through-connection of switches $S_1$ through $S_n$, and thus also an actuation of transducer elements $W_1$ through $W_n$, correspondingly in quintuplets. Thus, the result is ultrasonic scanning in even-numbered lines $Z_2$, $Z_4$, $Z_6$, etc. By superposing both subframe images on display unit 9, the full image frame 31 then results which, as previously mentioned, again comprises a total of 101 lines. With the interlaced scanning method according to the sample embodiment of FIG. 4, there is thus a resulting same number of lines as in the sample embodiment of FIG. 3, whereby, however, the image repetition frequency is doubled. Thus, with an electronic outlay which, in addition, has been further reduced, ultrasonic sectional images are obtained which are guaranteed to be always flicker-free.

With sample embodiments according to FIGS. 3 and 4, there is ultrasonic scanning specifically along one line. However, the scanning method according to the invention can also be readily carried out in an areal or surface manner. For this purpose, it is only necessary to replace the linear array of transducer elements $W_1$ through $W_3$ according to sample embodiments of FIGS. 3 and 4 with a corresponding areal array. In the case of an areal array of transducer elements such as this, the area-scanning may proceed according to any desired scheme or plan; for example, in linear fashion, in column fashion, or in a mixed procedure consisting of both. What is important is only that the respective transducer groups be sequentially activated in the one as well as in the other areal direction in accordance with one of the procedures described, for example, with regard to FIGS. 3 and 4. Areal arrays constructed and actuated in this manner require a total outlay of transducer elements and electronic actuating switches which is only one-fourth of the outlay required in the case of comparable areal arrays of a conventional nature. In the sample embodiments according to FIGS. 3 and 4, actuation of transducer elements preferably proceeds in quadruplets or quintuplets of adjacent transducer elements, whereby the individual groups border on one another or even overlap with one another in the sequence of actuation. However, a scanning plan such as this with conditions of this type is only exemplary and not compulsory for the general execution of the inventive scanning procedure; on the contrary, the inventive scanning procedure may also be carried out with separate individual or randomly group-associated transducer elements of the entire transducer element arrangement, provided that the selected symmetric transducer configurations, in accordance with the invention, exhibit such symmetry axes which do in fact permit occupation of transmitting/receiving directions in every possible position in the gaps between two transducer elements, and in the centers of the transducer elements. Examples of different symmetric transducer configurations with an even-numbered and/or odd-numbered count of transducer elements which satisfy these requirements are schematically indicated by way of example in FIGS. 5 and 6. Respective simultaneously energized transducer elements of a group configuration are represented with hatching.

It will be apparent that many modifications and variations may be effected without departing from the scope of the novel concepts and teachings of the present invention.

I claim as my invention:

1. Apparatus for examining bodies through scanning by means of ultrasound, comprising an ultrasonic applicator with at least one row of adjacent ultrasonic transducer elements, and an actuating mechanism for group-actuation of the transducer elements, characterized in that the actuating mechanism for actuating the transducer elements of the ultrasonic applicator comprises means for actuating different symmetric configurations of transducer elements having different types of symmetry axes in a predetermined sequence during a complete scanning cycle, the different symmetric configurations of simultaneously energized transducer elements comprising first configurations each with a first type of symmetry axis where the symmetry axis is positioned between two adjacent transducer elements, and comprising second configurations of simultaneously energized transducer elements with a second type of symmetry axis where the symmetry axis is positioned at the center of a transducer element.

2. Apparatus according to claim 1, with the first configuration of simultaneously energized transducer elements comprising even-numbered counts of transducer elements, the second configurations of simultaneously energized transducer elements comprising odd numbered counts of transducer elements, and the actuating mechanism alternately actuating the first and second configurations of transducer elements.

3. Apparatus according to claim 1, with the first configurations of simultaneously energized transducer elements such comprising an even-numbered count of transducer elements, the second configurations of simultaneously energized transducer elements each comprising an odd-numbered count of transducer elements, and the actuating mechanism actuating successive ones of said first configurations of transducer elements in a first cycle and actuating successive ones of said second configurations of transducer elements in a second cycle, the first and second cycles together providing a total image formed from interlaced sub-images corresponding to the different symmetric configurations.

4. Apparatus according to claim 1, with respective group program generators for supplying different numbers of pulses in accordance with the respective numbers of simultaneously energized transducer elements of the different symmetric configurations.

5. Apparatus according to claim 1 with the actuating mechanism comprising switches associated with the respective transducer elements for activating the same, shift registers for controlling the switches to respectively activate first configurations of said transducer elements and second configurations of said transducer elements, a first program generator for supplying an odd numbered count to a first of said shift registers so as to activate odd-numbered counts of transducer elements, and a second program generator for introducing an even-numbered count to a second of said shift registers for activating even-numbered counts of said transducer elements, the counts in said shift registers being shiftable as a group therein so as to sequentially activate first configurations of odd-numbered counts of transducer elements and second configurations of even-numbered counts of transducer elements during a complete scanning cycle of the actuating mechanism.

6. Apparatus according to claim 1 with the actuating mechanism comprising a shift register having a number of register positions corresponding to the number of transducer elements, means for introducing a first group of pulses to produce first configurations of simultaneously energized transducer elements as the first group is shifted in the shift register, and for introducing a second group of pulses into the shift register for activating second configurations of simultaneously energized transducer elements as the second group is shifted through the shift register.

7. Apparatus according to claim 1 with said actuating mechanism comprising a common shift register with program generator means for selectively loading an even-numbered pulse group and an odd-numbered pulse group into said common shift register to correspond respectively to the first configuration of transducer elements and the second configuration of transducer elements, the shift register being operable to shift the even-numbered pulse group therethrough to produce a first cycle of scanning by the ultrasonic applicator and being operable to shift the odd-numbered pulse group therethrough in a second cycle for activating successive second configurations of the transducer elements, the first and second cycles producing scanning along respective first and second axes of symmetry which are interlaced with respect to each other.

8. Apparatus according to claim 1 with the actuating mechanism being operable for generating a number of scanning lines, N, the ultrasonic applicator having a number of transducer elements less than N.

9. Apparatus according to claim 8 where the applicator has a length L, with each transducer element having a width of approximately 2 L/N, and with a gap distance of at least about 0.2 mm between adjacent transducer elements.

10. Apparatus according to claim 9 with said actuating mechanism having a number of switches for individually activating the respective transducer elements corresponding approximately to N/2.

* * * * *